US010570382B2

(12) United States Patent
Cooper et al.

(10) Patent No.: US 10,570,382 B2
(45) Date of Patent: Feb. 25, 2020

(54) TRANSPOSASE POLYPEPTIDES AND USES THEREOF

(71) Applicant: BOARD OF REGENTS, THE UNIVERSITY OF TEXAS SYSTEM, Austin, TX (US)

(72) Inventors: Laurence J. N. Cooper, Houston, TX (US); Natalya Belousova, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 128 days.

(21) Appl. No.: 15/556,868

(22) PCT Filed: Mar. 10, 2016

(86) PCT No.: PCT/US2016/021693
§ 371 (c)(1),
(2) Date: Sep. 8, 2017

(87) PCT Pub. No.: WO2016/145146
PCT Pub. Date: Sep. 15, 2016

(65) Prior Publication Data
US 2018/0051265 A1 Feb. 22, 2018

Related U.S. Application Data

(60) Provisional application No. 62/131,827, filed on Mar. 11, 2015.

(51) Int. Cl.
*C12N 1/20* (2006.01)
*C12N 9/22* (2006.01)
*A61K 48/00* (2006.01)

(52) U.S. Cl.
CPC ............. *C12N 9/22* (2013.01); *A61K 48/00* (2013.01)

(58) Field of Classification Search
CPC .................................. C12N 15/90; C12N 9/22
USPC ....................................................... 435/183
See application file for complete search history.

(56) References Cited

U.S. PATENT DOCUMENTS

| 6,489,458 B2 | 12/2002 | Hackett et al. |
| 2006/0026699 A1* | 2/2006 | Largaespada ........ C12Q 1/6876 800/10 |
| 2011/0117072 A1 | 5/2011 | Izsvak et al. |

FOREIGN PATENT DOCUMENTS

| WO | WO 2017/048902 | 3/1917 |
| WO | WO 2017/075147 | 5/1917 |
| WO | WO 03/089618 | 10/2003 |
| WO | WO 2010/008564 | 1/2010 |
| WO | WO 2013/074916 | 5/2013 |
| WO | WO 2014/186469 | 11/2014 |
| WO | WO 2014/190273 | 11/2014 |
| WO | WO 2015/061694 | 4/2015 |
| WO | WO 2015/123642 | 8/2015 |
| WO | WO 2015/164594 | 10/2015 |
| WO | WO 2015/164740 | 10/2015 |
| WO | WO 2016/073629 | 5/2016 |
| WO | WO 2016/073755 | 5/2016 |
| WO | WO 2016/138091 | 9/2016 |

OTHER PUBLICATIONS

International Preliminary Report on Patentability issued in International Application No. PCT/US2016/021693, dated Sep. 21, 2017.
International Search Report and Written Opinion issued in International Application No. PCT/US2016/021693, dated Jul. 26, 2016.
Invitation to Pay Additional Fees and Partial Search Report issued in International Application No. PCT/US2016/021693, dated May 19, 2016.
Ivics, Zoltán, et al. "Molecular reconstruction of Sleeping Beauty, a Tcl-like transposon from fish, and its transposition in human cells." Cell 91.4 (1997): 501-510.
Mátés, Lajos, et al. "Molecular evolution of a novel hyperactive Sleeping Beauty transposase enables robust stable gene transfer in vertebrates." Nature genetics 41.6 (2009): 753.

\* cited by examiner

*Primary Examiner* — Tekchand Saidha
(74) *Attorney, Agent, or Firm* — Parker Highlander PLLC

(57) ABSTRACT

Transposase polypeptides and polynucleotides are provided, which have a high activity in mammalian cells. Methods for engineering cells, such as chimeric antigen T-cells, with the transposes are also provided.

20 Claims, 2 Drawing Sheets
Specification includes a Sequence Listing.

SEQUENCE LISTING

<160> NUMBER OF SEQ ID NOS: 7

<210> SEQ ID NO 1
<211> LENGTH: 340
<212> TYPE: PRT
<213> ORGANISM: Artificial Sequence
<220> FEATURE:
<223> OTHER INFORMATION: Synthetic polypeptide

<400> SEQUENCE: 1

```
Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Arg Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys His Val Arg Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```

<210> SEQ ID NO 2
<211> LENGTH: 1023
<212> TYPE: DNA
<213> ORGANISM: Artificial Sequence
<220> FEATURE:
<223> OTHER INFORMATION: Synthetic polynucleotide

<400> SEQUENCE: 2

```
atgggcaaga gcaaagagat cagccaggac ctgcggaagc ggatcgtgga cctgcacaag      60
agcggctcta gcctgggcgc catcagcaag agactggccg tgcctagaag cagcgtgcag     120
accatcgtgc ggaagtacaa gcaccacggc accacccagc ccagctacag atctggaagg     180
cggagagtgc tgagcccag ggacgagaga acactcgtgc gcaaggtgca gatcaacccc     240
cggaccaccg ccaaggacct cgtgaagatg ctggaagaga caggcaccaa ggtgtccatc     300
agcaccgtga agcgggtgct gtaccggcac aacctgaagg ccacagcgc cagaaagaag     360
cccctgctgc agaacagaca caagaaggcc cggctgagat cgccagagc ccacggcgac     420
aaggacagaa ccttctggcg gaacgtgctg tggagcgacg agacaaagat cgagctgttc     480
ggccacaacg accacagata cgtgtggcgg aagaagggcg aggcctgcaa gcccaagaac     540
accatcccca cagtgaagca cggcggaggc agcatcatgc tgtggggctg ttttgccgct     600
ggcggcacag gcgccctgca caaaatcgac ggcatcatgg acgccgtgca gtacgtggac     660
atcctgaagc agcaccctgaa aacctctgtg cggaagctga agctgggccg gaaatgggtg     720
ttccagcacg acaacgaccc caagcacacc agcaagcacg tgcggaaatg gctgaaggac     780
aacaaagtga agtgctgga atggcccagc cagtcccccg acctgaaccc catcgaaaac     840
ctgtgggccg agctgaagaa aagagtgcgg gccagacggc ccaccaacct gacacagctg     900
caccagctgt gccaggaaga gtgggccaag atccacccca actactgcgg caagctggtg     960
gaaggctacc ccaagaggct gacccaagtg aaacagttca agggcaacgc caccaagtac    1020
tga                                                                  1023
```

<210> SEQ ID NO 3
<211> LENGTH: 340
<212> TYPE: PRT
<213> ORGANISM: Artificial Sequence
<220> FEATURE:
<223> OTHER INFORMATION: Synthetic polypeptide

<400> SEQUENCE: 3

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

```
Lys Ala Arg Leu Arg Phe Ala Arg Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Ser Ile
            180                 185                 190

Met Leu Trp Gly Cys Phe Ala Ala Gly Gly Thr Gly Ala Leu His Lys
            195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys His Val Arg Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 4
<211> LENGTH: 1023
<212> TYPE: DNA
<213> ORGANISM: Artificial Sequence
<220> FEATURE:
<223> OTHER INFORMATION: Synthetic polynucleotide

<400> SEQUENCE: 4
atgggcaaga gcaaagagat cagccaggac ctgcggaagc ggatcgtgga cctgcacaag     60
agcggctcta gcctgggcgc catcagcaag agactggccg tgcctagaag cagcgtgcag    120
accatcgtgc ggaagtacaa gcaccacggc accacccagc ccagctacag atctggaagg    180
cggagagtgc tgagcccag ggacgagaga acactcgtgc gcaaggtgca gatcaacccc    240
cggaccaccg ccaaggacct cgtgaagatg ctggaagaga caggcaccaa ggtgtccatc    300
agcaccgtga gcgggtgct gtaccggcac aacctgaagg ccacagcgc cagaaagaag    360 cccctgctgc agaacagaca caagaaggcc cggctgagat cgccagagc ccacggcgac    420 aaggacagaa ccttctggcg gaacgtgctg tggagcgacg agacaaagat cgagctgttc    480
ggccacaacg accacagata cgtgtggcgg aagaagggcg aggcctgcaa gcccaagaac    540
accatcccca cagtgaagca cggcggaggc agcatcatgc tgtggggctg ttttgccgct    600
ggcggcacag gcgccctgca caaaatcgac ggcatcatgg acgccgtgca gtacgtggac    660
atcctgaagc agcacctgaa aacctctgtg cggaagctga gctgggccg gaaatgggtg    720 ttccagcacg acaacgaccc caagcacacc agcaagcacg tgcggaaatg ctgaaggac    780 aacaaagtga agtgctgga atggcccagc cagtcccccg acctgaaccc catcgaaaac    840
```

-continued

```
ctgtgggccg agctgaagaa aagagtgcgg gccagacggc ccaccaacct gacacagctg    900
caccagctgt gccaggaaga gtgggccaag atccacccca cctactgcgg caagctggtg    960
gaaggctacc ccaagaggct gacccaagtg aaacagttca agggcaacgc caccaagtac   1020
tga                                                                 1023
```

<210> SEQ ID NO 5
<211> LENGTH: 340
<212> TYPE: PRT
<213> ORGANISM: Artificial Sequence
<220> FEATURE:
<223> OTHER INFORMATION: Synthetic polypeptide

<400> SEQUENCE: 5

```
Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Arg Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Gln Asp Asn Asp Pro Lys His Thr Ser Lys His Val Arg Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320
```

```
Glu Gly Tyr Pro Lys Arg Leu Thr Gln Val Lys Gln Phe Lys Gly Asn
            325                 330                 335

Ala Thr Lys Tyr
            340

<210> SEQ ID NO 6
<211> LENGTH: 340
<212> TYPE: PRT
<213> ORGANISM: Artificial Sequence
<220> FEATURE:
<223> OTHER INFORMATION: Synthetic polypeptide

<400> SEQUENCE: 6

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335
```

Ala Thr Lys Tyr
            340

<210> SEQ ID NO 7
<211> LENGTH: 340
<212> TYPE: PRT
<213> ORGANISM: Artificial Sequence
<220> FEATURE:
<223> OTHER INFORMATION: Synthetic polypeptide

<400> SEQUENCE: 7

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

TRANSPOSASE POLYPEPTIDES AND USES THEREOF

This application is a national phase application under 35 U.S.C. § 371 of International Application No. PCT/US2016/021693, filed Mar. 10, 2016, which claims the benefit of U.S. Provisional Application 62/131,827, filed on Mar. 11, 2016, the entire content of each of which is incorporated herein by reference.

INCORPORATION OF SEQUENCE LISTING

The sequence listing that is contained in the file named "UTFCP1256WO_ST25.txt", which is 18 KB (as measured in Microsoft Windows®) and was created on Mar. 3, 2016, is filed herewith by electronic submission and is incorporated by reference herein.

BACKGROUND OF THE INVENTION

1. Field of the Invention

The present invention relates generally to the fields of medicine, immunology, cell biology, and molecular biology. In certain aspects, the field of the invention concerns transposase polypeptides and the used thereof in genetic engineering.

2. Description of Related Art

In the era of functional genomics, there is a need for efficient means to alter the coding sequence in the genome of cells. Such genome engineering can be used to produce cells with stably expressed transgenes and for cell reprogramming. One suitable tool used in genome engineering is transposon/transposase systems. Transposons or transposable elements include a (short) nucleic acid sequence with terminal repeat sequences upstream and downstream thereof and encode enzymes that facilitate the excision and insertion of the nucleic acid into target DNA sequences. Several transposon/transposase systems have been adapted for genetic insertions of heterologous DNA sequences, including Sleeping Beauty (SB), a Tc1/mariner-like element from fish that exhibits transpositional activity in a variety of vertebrate cultured cell lines, embryonic stem cells and in vivo (Ivics et al., 1997). However, none of these systems has been adopted for human/mammalian cells engineering. Accordingly, there is need for transposon/transposase systems with a high level of activity in mammalian cells and organisms.

SUMMARY OF THE INVENTION

In a first embodiment is provided a recombinant polypeptide comprising or consisting of enhanced transposase activity in mammalian cells. In some aspects, a polypeptide of the embodiments comprises or consists of a sequence at least 90% identical to SEQ ID NO: 1 (hSB110) or SEQ ID NO: 3 (hSB81). In certain aspects, a polypeptide comprises or consists of a sequence of SEQ ID NO: 1 or SEQ ID NO: 3 or a sequence at least 90% identical to the full length of SEQ ID NO: 1 or SEQ ID NO:3 and exhibits transposase activity in mammalian cells. In a further aspect, the polypeptide comprises or consists of a sequence at least 90% identical to SEQ ID NO: 1 or SEQ ID NO:3, exhibits transposase activity in mammalian cells, and comprises one or more of the following features: an Arg at the position corresponding to position 136 (in hSB110), a His at the position corresponding to position 253 (in hSB110), an Arg at the position corresponding to position 255 (in hSB110) and/or a Thr at the position corresponding to position 314 (in hSB110). In further aspects, the preceding at least 90% identical polypeptide does not comprise the sequence of a naturally occurring transposase enzyme or does not comprise the sequence of SEQ ID NO: 5 (SB11), SEQ ID NO: 6 (SB10) or SEQ ID NO: 7 (SB100x). In some aspects, a polypeptide of the embodiments comprises or consists of a sequence at least 91%, 92%, 93%, 94%, 95%, 96%, 97%, 98% or 99% identical to SEQ ID NO: 1 (hSB110) or SEQ ID NO: 3 (hSB81). In some aspects, a polypeptide of the embodiments comprises or consists of a sequence at least 91%, 92%, 93%, 94%, 95%, 96%, 97%, 98% or 99% identical to SEQ ID NO: 1 (hSB110) or SEQ ID NO: 3 (hSB81) and exhibits transposase activity in mammalian cells. In some aspects, a polypeptide of the embodiments comprises or consists of a sequence at least 91%, 92%, 93%, 94%, 95%, 96%, 97%, 98% or 99% identical to SEQ ID NO: 1 (hSB110) or SEQ ID NO: 3 (hSB81), exhibits transposase activity in mammalian cells, and comprises or consists of one or more of the following features: an Arg at the position corresponding to position 136 (in hSB110), a His at the position corresponding to position 253 (in hSB110), an Arg at the position corresponding to position 255 (in hSB110) and/or a Thr at the position corresponding to position 314 (in hSB110). In some aspects, the preceding at least 91%, 92%, 93%, 94%, 95%, 96%, 97%, 98% or 99% identical polypeptide does not comprise the sequence of a naturally occurring transposase enzyme or does not comprise the sequence of SEQ ID NO: 5 (SB11), SEQ ID NO: 6 (SB10) or SEQ ID NO: 7 (SB100x). In yet further aspects, a transposase polypeptide of the embodiments further comprises or consists of a heterologous polypeptide sequence fused to the N- or C-terminus of the transposase sequence. For example, the heterologous polypeptide sequence may comprise or consist of a reporter, a purification tag or a cell penetrating polypeptide (CPP). In further aspects, the mammalian cell in which polypeptides of the embodiments exhibit transposase activity are human cells. In further aspects, the human cells are immune cells. In further aspects the human immune cells are T cells. In further aspects, the T cells are T helper cells ($T_H$ cells), cytotoxic T cells ($T_c$ cells or CTLs), memory T cells ($T_{CM}$ cells), effector T cells ($T_{EM}$ cells), regulatory T cells (Treg cells; also known as suppressor T cells), natural killer T cells (NKT cells), mucosal associated invariant T cells, alpha-beta T cells (Tαβ cells), and/or gamma-delta T cells (Tγδ cells).

In yet a further aspect, a polypeptide of the embodiments comprises or consists of a sequence at least 90%, 91%, 92%, 93%, 94%, 95%, 96%, 97%, 98% or 99% identical to SEQ ID NO: 1 (hSB110) or SEQ ID NO: 3 (hSB81), comprises one or more of the following features: an Arg at the position corresponding to position 136 (in hSB110), a His at the position corresponding to position 253 (in hSB110), an Arg at the position corresponding to position 255 (in hSB110) and/or a Thr at the position corresponding to position 314 (in hSB110) and further comprises one or more of the following additional features: an Arg at the position corresponding to position 14 (in hSB110), an Ala at the position corresponding to position 33 (in hSB110), a His at the position corresponding to position 115 (in hSB110), an Asp at the position corresponding to position 214 (in hSB110), an Ala at the position corresponding to position 215 (in hSB110), a Val at the position corresponding to position 216 (in hSB110), a Gln at the position corresponding to position 217

(in hSB110), and/or a His at the position corresponding to position 243 (in hSB110). In some aspects, the preceding at least 90%, 91%, 92%, 93%, 94%, 95%, 96%, 97%, 98% or 99% identical polypeptide does not comprise the sequence of a naturally occurring transposase enzyme or does not comprise the sequence of SEQ ID NO: 5 (SB11), SEQ ID NO: 6 (SB10) or SEQ ID NO: 7 (SB100x). In some aspects, a polypeptide of the embodiments comprises 2, 3, 4, 5, 6, 7 or 8 of the sequence features selected from the group consisting of: an Arg at the position corresponding to position 14 (in hSB110), an Ala at the position corresponding to position 33 (in hSB110), a His at the position corresponding to position 115 (in hSB110), an Asp at the position corresponding to position 214 (in hSB110), an Ala at the position corresponding to position 215 (in hSB110), a Val at the position corresponding to position 216 (in hSB110), a Gln at the position corresponding to position 217 (in hSB110), and a His at the position corresponding to position 243 (in hSB110). In further aspects, the preceding at least 90%, 91%, 92%, 93%, 94%, 95%, 96%, 97%, 98% or 99% identical polypeptide comprises the sequence DAVQ at the positions corresponding to positions 214-217 (in hSB110).

In some aspects, the polypeptide of the embodiments comprises or consists of a sequence at least 90%, 91%, 92%, 93%, 94%, 95%, 96%, 97%, 98% or 99% identical to SEQ ID NO: 1 (hSB110), comprises a Asn at the position corresponding to position 314 (in hSB110) and comprises one or more of the following features: an Arg at the position corresponding to position 136 (in hSB110), a His at the position corresponding to position 253 (in hSB110), and/or an Arg at the position corresponding to position 255 (in hSB110). In some aspects, the preceding at least 90%, 91%, 92%, 93%, 94%, 95%, 96%, 97%, 98% or 99% identical polypeptide does not comprise the sequence of a naturally occurring transposase enzyme or does not comprise the sequence of SEQ ID NO: 5 (SB11), SEQ ID NO: 6 (SB10) or SEQ ID NO: 7 (SB100x). In specific aspects, the polypeptide comprises or consists of the sequence of SEQ ID NO: 1.

In other aspects, the polypeptide of the embodiments comprises or consists of a sequence at least 90%, 91%, 92%, 93%, 94%, 95%, 96%, 97%, 98% or 99% identical to SEQ ID NO: 3 (hSB81), comprises a Thr at the position corresponding to position 314 (in hSB110) and comprises one or more of the following features: an Arg at the position corresponding to position 136 (in hSB110), a His at the position corresponding to position 253 (in hSB110), and/or an Arg at the position corresponding to position 255 (in hSB110). In some aspects, the preceding at least 90%, 91%, 92%, 93%, 94%, 95%, 96%, 97%, 98% or 99% identical polypeptide does not comprise the sequence of a naturally occurring transposase enzyme or does not comprise the sequence of SEQ ID NO: 5 (SB11), SEQ ID NO: 6 (SB10) or SEQ ID NO: 7 (SB100x). In specific aspects, the polypeptide comprises or consists of the sequence of SEQ ID NO: 3.

In a further embodiment there is provided a polynucleotide molecule comprising or consisting of a sequence encoding a polypeptide according to the embodiments. The molecule may be a DNA expression vector in some aspects. For example, the DNA expression vector may comprise a transposase coding sequence operably linked to a promoter for in vitro expression of the polypeptide (e.g., a T7 or SP6 promoter) or a promoter for expression of the polypeptide in mammalian cells. In some aspects, the polynucleotide molecule may be a RNA or mRNA. In further aspects, the RNA may comprise a 5'-cap, an IRES motif, a (heterologous) 5' UTR, a (heterologous) 3' UTR and/or a poly(A) sequence. The RNA may additionally comprise a poly(A) sequence of 20 to 300 nucleotides in some aspects.

In yet a further embodiment the invention provides a method of making a transposase polypeptide as described above, comprising transfecting a cell with a polynucleotide encoding a transposase polypeptide and expressing the polypeptide from the polynucleotide. In still a further embodiment, the invention provides a host cell comprising a polypeptide or a polynucleotide molecule of the embodiments. In some cases, the cell is a mammalian cell, such as a human cell. In certain aspects, the cell is a stem cell or an induced pluripotent stem (iPS) cell. In further aspects, the cell is a natural killer (NK) cell, a precursor of a NK cell, a T-cell, a precursor of a T-cell, or an immune cell. In some cases, the cell may comprise a RNA encoding a transposase polypeptide of the embodiments. In yet further embodiments a population of cells, said cells comprising polypeptide or a polynucleotide molecule of the embodiments, is provided.

In another embodiment, a method is provided for genetically engineering a cell comprising: transfecting the cell with a transposase polypeptide as described above or a nucleic acid encoding the transposase polypeptide and a DNA vector comprising a sequence encoding a selected genetic element flanked by transposon repeats, then incubating the cell under conditions appropriate for (transient or stable) transposase activity, thereby integrating the selected genetic element in the genome of the cell and producing an engineered cell. In certain aspects, a DNA vector encoding a selected genetic element flanked by transposon repeats further comprises a sequence encoding a transposase polypeptide of the embodiments. Thus, in certain aspects, a method of the embodiments comprises transfecting a cell with a DNA vector comprising a sequence encoding a selected genetic element flanked by transposon repeats and a sequence encoding a transposase of the embodiments, which is under the control of a promoter sequence, then incubating the cell under conditions appropriate for transposase expression and activity, thereby integrating the selected genetic element in the genome of the cell and producing an engineered cell. In some aspects, the method comprises the third step of isolating or culturing the engineered cell. In some aspects, the selected genetic element is a screenable or selectable marker. In further aspects, the selected genetic element may encode an antibody, a inhibitory nucleic acid (e.g., a small interfering RNA (siRNA)), a therapeutic polypeptide, a T-cell receptor (TCR), a chimeric antigen receptor (CAR), or an enhancer of immune cell function. In specific aspects, the selected genetic element encodes a CAR or TCR. In still further aspects, the selected genetic element may be a gene or a portion thereof that is used to replace or modify the corresponding gene from a cell (e.g., to alter the sequence or expression of the gene or to "knock-out" gene expression in the cell). In some aspects, the transfected cell is a mammalian cell such as human cell. In some cases, the cell may be a stem cell or an iPS cell. In certain aspects, the cell may be an immune system cell or a precursor thereof, such as a NK cell, a T-cell, a precursor of a NK cell, or a precursor of a T-cell.

In some aspects, transfecting cells may comprise use of a chemical-based transfection reagent, electroporation of the cells or other technologies providing delivery of nucleic acid and/or protein to the cytoplasm and nucleus of cells. For example, cells can be transfected using salt precipitates (e.g., $CaPO_4$ precipitates), lipids (e.g., charged or non-polar lipids), cationic polymers, PEG-complexes and/or protein complexes (e.g., cationic polypeptides). In some aspects, transfections may involve the use of liposomes, such as phospholipid liposomes (e.g., liposomes that incorporate a glycerophospholipid or sphingolipids). In still further aspects, cells may be transduced with a viral vector (e.g., adenoviral, adeno-associated viral, retroviral (e.g., lentiviral) or vaccinia virus vector). In certain aspects, a viral vector for use according to the embodiments is a non-integrating viral vector. A skilled artisan will recognize that, in certain aspects, a transposase of the embodiments may be delivered to cells together or separately from a nucleic acid encoding transposon repeats. For example, in certain aspects, a transposase may be delivered to cells as a recombinant polypeptide using a protein transfection reagent and the nucleic acid molecule comprising the transposon repeats can be delivered using a nucleic acid transfection system or a viral vector. In further aspects, an RNA encoding a transposase is co-transfected with a DNA comprising transposon repeats and a selected genetic element.

In further aspects, the method additionally comprises transfecting a population of cells with a transposase polypeptide of the embodiments or a nucleic acid encoding the transposase polypeptide and a DNA vector comprising a sequence encoding a selected genetic element flanked by transposon repeats and then incubating the population under conditions appropriate for transposase activity, thereby integrating the selected genetic element in the genome of the cells and producing a population of engineered cells. In specific aspects, the method comprises transfecting a population of T-cells, or T-cell precursors, with a transposase polypeptide or a nucleic acid encoding the transposase polypeptide and a DNA vector comprising a sequence encoding a CAR flanked by transposon repeats and incubating the population under conditions appropriate for transposase activity, thereby integrating the CAR in the genome of the cells and producing a population of engineered T-cells, or T-cell precursors. In further aspects, the method comprises transfecting a population of T-cells, or T-cell precursors, with a DNA vector comprising a sequence encoding a CAR flanked by transposon repeats and a sequence encoding a transposase of the embodiments (operably linked to a promoter) and incubating the population under conditions appropriate for transposase activity, thereby integrating the CAR in the genome of the cells and producing a population of engineered T-cells, or T-cell precursors. Culturing the engineered cells in a medium that selectively enhances proliferation of CAR-expressing T-cells may be additionally performed in some aspects.

In yet a further embodiment there is provided a method of providing a T-cell response in a human subject having a disease comprising first obtaining a population of engineered T-cells, or T-cell precursors, in accordance with the embodiments, optionally culturing the cells in a medium that selectively enhances proliferation of CAR-expressing T-cells, and then administering an effective amount of the CAR-expressing T-cells to the subject to provide a T-cell response.

Thus, in some aspects, a method of the embodiments comprises: (a) obtaining a sample of cells from the subject, the sample comprising T-cells or T-cell progenitors; (b) transfecting the cells with a DNA encoding a transposon-flanked chimeric antigen receptor (CAR) and a transposase of the embodiments effective to integrate the DNA encoding the CAR into the genome of the cells, to provide a population of transgenic CAR-expressing cells; (c) optionally, culturing the population of transgenic CAR cells ex vivo in a medium that selectively enhances proliferation of CAR-expressing T-cells; and (d) administering an effective amount of the transgenic CAR cells to the subject to provide a T-cell response. Thus, in some aspects, the transgenic CAR cells are cultured ex vivo for less than 21 days, such as for less than 20, 19, 18, 17, 16, 15, 14, 13, 12, 11, 10, 9, 8, 7, 6, 5, 4, 3, 2 days or less. In certain aspects, the CAR cells are cultured ex vivo no more that 3 to 5 days. In still further aspects, steps (a)-(d) of the instant method (i.e., obtaining cell samples to administering CAR T cells) are completed in no more than 21, 20, 19, 18, 17, 16, 15, 14, 13, 12, 11, 10, 9, 8, 7, 6, or 5 days. In further aspects, the sample of cells from the subject may be a sample of less than about 200 mls of a peripheral blood or umbilical cord blood. In some aspects, the sample may be collected by apheresis. In certain aspects, the sample is collected by a method that does not involved apheresis (e.g., by venipuncture). In still further aspects, the sample of cells has an initial volume of less than 175 mls, less than about 175 mls, less than 150 mls, less than about 150 mls, less than 125 mls, less than about 125 mls, less than 100 mls, less than about 100 mls, less than 75 mls, less than about 75 mls, less than 50 mls, less than about 50 mls, less than 25 mls, or less than about 25 mls (e.g., the sample of cells has an initial volume of between about 50 and about 200 mls, between about 50 and about 100 mls, or between about 100 and about 200 mls when obtained from the subject).

In some aspects, methods of the embodiments concern transfecting the cells with a DNA encoding a chimeric antigen receptor (CAR) and a transposase. Methods of transfecting of cells are well known in the art, but in certain aspects, highly efficient transfections methods such as electroporation are employed. For example, nucleic acids may be introduced into cells using a nucleofection apparatus. In certain embodiments, the transfection step does not involve infecting or transducing the cells with virus, which can cause genotoxicity and/or lead to an immune response against cells containing viral sequences in a treated subject.

Further aspects of the embodiments concern transfecting cells with an expression vector encoding a CAR. A wide range of CAR constructs and expression vectors for the same are known in the art. For example, in some aspects, the CAR expression vector is a DNA expression vector such as a plasmid, linear expression vector or an episome. In some aspects, the vector comprises additional sequences, such as sequence that facilitate expression of the CAR, such a promoter, enhancer, poly-A signal, and/or one or more introns. In certain aspects, the CAR coding sequence is flanked by transposon sequences, such that the presence of a transposase allows the coding sequence to integrate into the genome of the transfected cell.

As detailed supra, in certain aspects, cells are further transfected with a transposase of the embodiments that facilitates integration of a CAR coding sequence into the genome of the transfected cells. In some aspects, the transposase is provided as DNA expression vector. In certain aspects, the transposase is provided as an expressible RNA or a protein such that long-term expression of the transposase does not occur in the transgenic cells. For example, in some aspects, the transposase is provided as encoded by an mRNA (e.g., an mRNA comprising a cap and poly-A tail).

In still further aspects, a transgenic CAR cell of the embodiments further comprises an expression vector for expression of a membrane-bound cytokine that stimulates proliferation and/or survival of T-cells. In particular, CAR cells comprising such cytokines can proliferate and/or persist with little or no ex vivo culture with activating and propagating cells (AaPCs) or artificial antigen presenting cells (aAPCs) due to the simulation provided by the cytokine expression. Likewise, such CAR cells can proliferate in vivo even when large amounts of antigen recognized by the CAR is not present (e.g., as in the case of a cancer patient in remission or a patient with minimal residual disease). In some aspects, the CAR cells comprise a DNA or RNA expression vector for expression of a Cy cytokine and elements (e.g., a transmembrane domain) to provide surface expression of the cytokine. For example, the CAR cells can comprise membrane-bound versions of IL-7, IL-15 or IL-21. In some aspects, the cytokine is tethered to the membrane by fusion of the cytokine coding sequence with the receptor for the cytokine. For example, a cell can comprise a vector for expression of a IL-15-IL-15Rα fusion protein. In still further aspects, a vector encoding a membrane-bound Cy cytokine is a DNA expression vector, such as vector integrated into the genome of the CAR cells or an extra-chromosomal vector (e.g., and episomal vector). In still further aspects, expression of the membrane-bound Cy cytokine is under the control of an inducible promoter (e.g., a drug inducible promoter) such that the expression of the cytokine in the CAR cells (and thereby the proliferation of the CAR cells) can be controlled by inducing or suppressing promoter activity.

Aspects of the embodiments concern obtaining a sample from a patient comprising NK cells, NKT cells, T-cells or T-cell progenitor cells. For example, in some cases, the sample is an umbilical cord blood sample, a peripheral blood sample (e.g., a mononuclear cell fraction) or a sample from the subject comprising pluripotent stem cells. In some aspects, a sample from the subject can be cultured to generate induced pluripotent stem (iPS) cells and these cells used to produce NK cells, NKT cells or T-cells. Cell samples may be cultured directly from the subject or may be cryopreserved prior to use. In some aspects, obtaining a cell sample comprises collecting a cell sample. In other aspects, the sample is obtained by a third party. In still further aspects, a sample from a subject can be treated to purify or enrich the T-cells or T-cell progenitors in the sample. For example, the sample can be subjected to gradient purification, cell culture selection and/or cell sorting (e.g., via fluorescence-activated cell sorting (FACS)).

In some aspects, a method of the embodiments further comprises using antigen presenting cells (e.g., for expansion of engineered cells). For example, the antigen presenting cells can be dendritic cells, activating and propagating cells (AaPCs), or inactivated (e.g., irradiated) artificial antigen presenting cells (aAPCs). Methods for producing such antigen presenting cells are known in the art and further detailed herein. Thus, in some aspects, transgenic CAR cells are co-cultured with antigen presenting cells (e.g., inactivated aAPCs) ex vivo for a limited period of time in order to expand the CAR cell population. The step of co-culturing CAR cells can be done in a medium that comprises, for example, interleukin-21 (IL-21) and/or interleukin-2 (IL-2). In some aspects, the co-culturing is performed at a ratio of CAR cells to antigen presenting cells of about 10:1 to about 1:10; about 3:1 to about 1:5; or about 1:1 to about 1:3. For example, the co-culture of CAR cells and antigen presenting cells can be at a ratio of about 1:1, about 1:2 or about 1:3.

In some aspects, cells for culture of CAR cells such as AaPCs or aAPCs are engineered to express specific polypeptide to enhance growth of the CAR cells. For example, the cells can comprise (i) an antigen targeted by the CAR (i.e., that is expressed on the transgenic CAR cells); (ii) CD64; (ii) CD86; (iii) CD137L; and/or (v) membrane-bound IL-15, expressed on the surface of the aAPCs. In some aspects, the AaPCs or aAPCS comprise a CAR-binding antibody or fragment thereof expressed on the surface of the AaPCs or aAPCs. Preferably, AaPCs or aAPCs for use in the instant methods are tested for, and confirmed to be free of, infectious material and/or are tested and confirmed to be inactivated and non-proliferating.

While expansion on AaPCs or aAPCs can increase the number or concentration of CAR cells in a culture, this procedure is labor intensive and expensive. Moreover, in some aspects, a subject in need of therapy should be re-infused with transgenic CAR cells in as short a time as possible. Thus, in some aspects, ex vivo culturing the transgenic CAR cells is for no more than 14 days, no more than 7 days, or no more than 3 days. For example, the ex vivo culture (e.g., culture in the presence of AaPCs or aAPCs) can be performed for less than one population doubling of the transgenic CAR cells. In still further aspects, the transgenic cells are not cultured ex vivo in the presence of AaPCs or aAPCs.

In still further aspects, a method of the embodiments comprises a step for enriching the cell population for CAR-expressing T-cells after transfection of the cells or after ex vivo expansion of the cells. For example, the enrichment step can comprise sorting of the cells (e.g., via FACS), for example, by using an antigen bound by the CAR or a CAR-binding antibody. In still further aspects, the enrichment step comprises depletion of the non-T-cells or depletion of cells that lack CAR expression. For example, $CD56^+$ cells can be depleted from a culture population. In yet further aspects, a sample of CAR cells is preserved (or maintained in culture) when the cells are administered to the subject. For example, a sample may be cryopreserved for later expansion or analysis.

In certain aspects, transgenic CAR cells are inactivated for expression of an endogenous T-cell receptor and/or endogenous HLA. For example, T cells can be engineered to eliminate expression of endogenous alpha/beta T-cell receptor (TCR). In specific embodiments, $CAR^+$ T cells are genetically modified to eliminate expression of TCR. In some aspects, there is a disruption of the T-cell receptor α/β in CAR-expressing T cells using zinc finger nucleases (ZFNs). In certain aspects, the T-cell receptor αβ-chain in CAR-expressing T cells is knocked-out, for example, by using zinc finger nucleases.

As further detailed herein, CAR cells of the embodiments can be used to treat a wide range of diseases and conditions. Essentially any disease that involves the specific or enhanced expression of a particular antigen can be treated by targeting CAR cells to the antigen. For example, autoimmune diseases, infections, and cancers can be treated with methods and/or compositions of the invention. These include cancers, such as primary, metastatic, recurrent, sensitive-to-therapy, refractory-to-therapy cancers (e.g., chemo-refractory cancer). The cancer may be of the blood, lung, brain, colon, prostate, breast, liver, kidney, stomach, cervix, ovary, testes, pituitary gland, esophagus, spleen, skin, bone, and so forth (e.g., B-cell lymphomas or a melanomas). In the case of cancer treatment CAR cells typically target a cancer cell antigen (also known as a tumor-associated antigen (TAA)).

In still further aspects, transgenic CAR cells of the embodiments may be used to treat subject having minimal residual disease (e.g., a subject having very low amounts of CAR-targeted antigen present), such as cancer patients that are in apparent remission. Using new highly sensitive diagnostic techniques, cancer-associated antigens (or cancer cells) can be detected in patients that do not exhibit overt cancer symptoms. Such patients may be treated by the instant methods to eliminate residual disease by use of antigen-targeted CAR cells. In certain embodiments, transgenic CAR cells for targeting of residual disease further comprise expression of a membrane-bound proliferative cytokine, as these cells will retain the ability to expand in vivo despite the low amount of target antigen.

The processes of the embodiments can be utilized to manufacture (e.g., for clinical trials) $CAR^+$ T cells with binding specificity for various tumor antigens (e.g., CD19, ROR1, CD56, EGFR, CD33, CD123, c-met, GD2). $CAR^+$ T cells generated using this technology can be used to treat patients with leukemias (e.g., AML, ALL, CML), infections and/or solid tumors. For example, methods of the embodiments can be used to treat cell proliferative diseases, fungal, viral, bacterial or parasitic infections. Pathogens that may be targeted include, without limitation, *Plasmodium*, trypanosome, *Aspergillus, Candida*, HSV, RSV, EBV, CMV, JC virus, BK virus, or Ebola pathogens. Further examples of antigens that can be targeted by CAR cells of the embodiments include, without limitation, CD19, CD20, carcinoembryonic antigen, alphafetoprotein, CA-125, 5T4, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, meothelin, GD3, HERV-K, IL-11Ralpha, kappa chain, lambda chain, CSPG4, ERBB2, EGFRvIII, or VEGFR2. In certain aspects, method of the embodiments concern targeting of CD19 or HERV-K-expressing cells. For example, a HERV-K targeted CAR cell can comprise a CAR including the scFv sequence of monoclonal antibody 6H5. In still further aspects, a CAR of the embodiments can be conjugated or fused with a cytokine, such as IL-2, IL-7, IL-15, IL-21 or a combination thereof.

In some embodiments, methods are provided for treating an individual with a medical condition comprising the step of providing an effective amount of cells from the population of cells described herein, including more than once in some aspects, such as at least 1, 2, 3, 4, 5, 6, 7, 8, 9, 10, 11, 12, 13, 14, or more days apart. In specific aspects, the cancer is cancer of the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In certain aspects, the cancer is a lymphoma, leukemia, non-Hodgkin's lymphoma, acute lymphoblastic leukemia, chronic lymphoblastic leukemia, chronic lymphocytic leukemia, or B cell-associated autoimmune diseases.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Genetic Engineering of Cells

Genetic engineering of cells has emerged as a powerful technique for providing stable expression of desired genes in a wide range of cells. Recently, such technology has even been applied to cells used for therapeutic intervention in a range of disease conditions. For example, genetically engineered T-cells that express receptors targeted to a disease-associated antigen are currently in clinical trials as an anti-cancer therapy. Transposase systems are a desirable system for use in engineering, especially in the case of cells used as therapeutics, since they do not introduce heterologous genetic elements that are maintained in the cells, a common feature of virus-based engineering systems. However, high efficiency is needed to provide a sufficient number of engineered T-cells that are required for therapeutic intervention.

Studies herein demonstrate new recombinant transposase enzymes, termed hSB110 and hSB81, which exhibit significantly improved efficiency in engineering of human cells.

Figure 2:
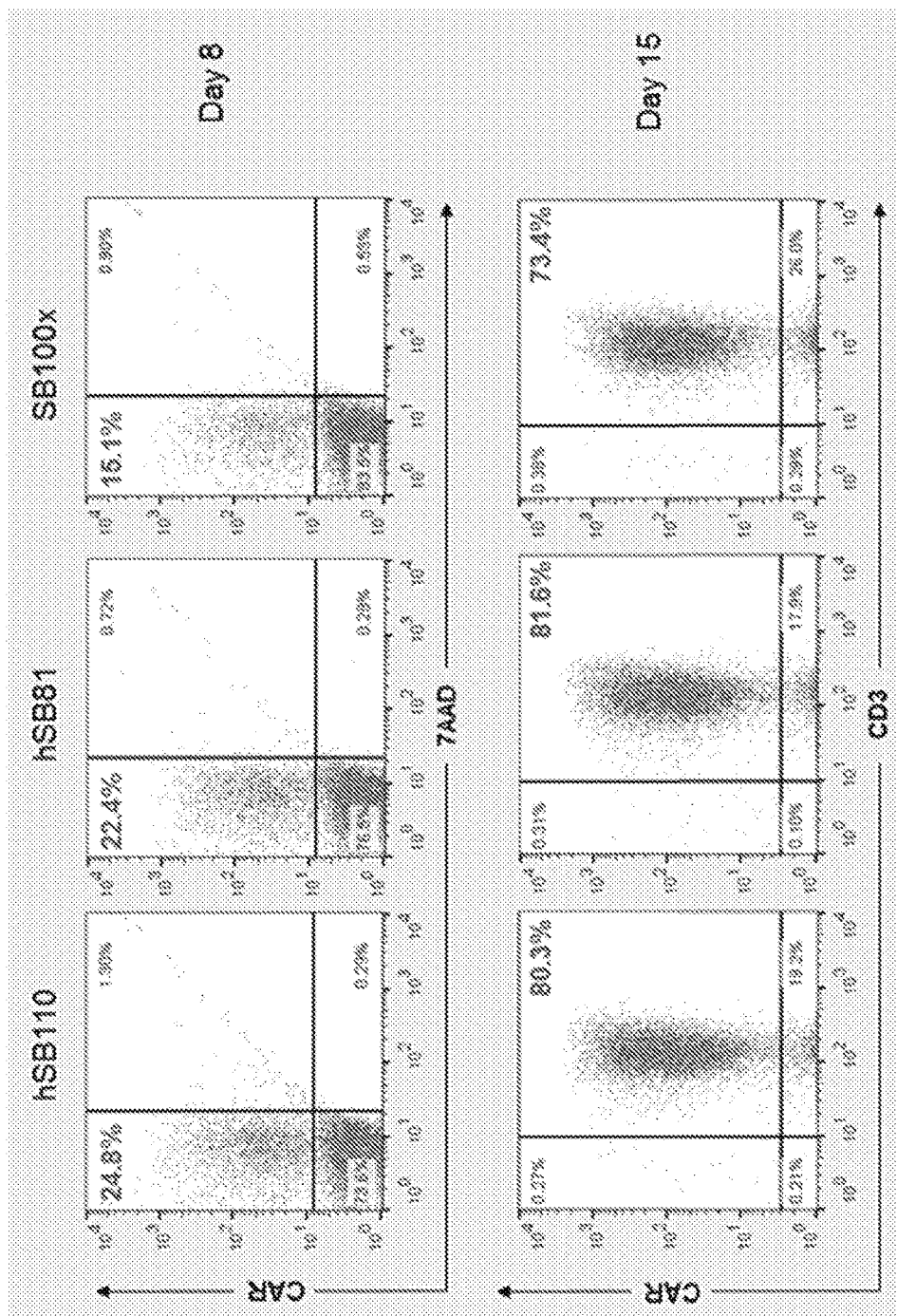
FIG. 2: Histograms show flow cytometry data of human T-cells transfected with CAR as outlined in FIG. 1. Results are compared between two recombinant transposases of the embodiments, hSB110 and hSB81, versus SB100x. Upper panels show the number of cells positive for CAR (y-axis) versus cells that have been rendered non-viable, as assessed by 7AAD (7-Aminoactinomycin D) staining (x-axis), 8-days post transfection. Lower panels show the number of cells positive for CAR expression (y-axis) and which express CD3 (x-axis), 15-days post transfection. Results of the studies show that the recombinant transposases of the embodiments are significantly more efficient at engineering cells than SB100x. By day 8 post transfection, over 22% of the cells electroporated with hSB110 and hSB81 coding mRNAs express CAR as compared to only 15% of cells resulting from the use of SB100x. Likewise, by day 15, over 80% of the cell population electroporated with hSB110 and hSB81 co-expressed CAR and CD3 as compared to only 73.4% of cells resulting from the use of SB100x.

For example, when used for integration of CAR expression constructs into primary human T-cells, the new transposases were able to produce populations of cells where well over 20% of the cells exhibited CAR expression by day 8 post transfection (FIG. 2). Moreover, by day 15, over 80% of the cells in the transfected population were positive for CAR expression (FIG. 2). Such high efficiency genetic engineering of human cells represents a significant improvement over previous transposase-based engineering systems.

Transposase coding sequences of the embodiments can be employed for high efficiency genetic engineering of mammalian cells. For example, the transposases can be used for rapid production of populations of CAR-expressing T-cells. In an embodiment, mRNA encoding the transposase is co-transfected into T-cells (or T-cell precursors) along with a DNA vector encoding the desired CAR expression cassette, flanked by transposon repeats. The CAR-expressing T-cells may then be purified and/or selectively expanded. In the case of T-cells used for therapy, it is desirable that as little expansion as possible be needed in order to reduce the time and cost of cell preparation. Importantly, the transposases provided herein significantly improve such an engineering procedure by increasing the proportion of cells that exhibit stable expression of the CAR and, which are therefore available for further expansion.

II. Transposase Polypeptides and Coding Sequences

As described in the foregoing summary, certain aspects of the embodiments concern recombinant transposase polypeptides and nucleic acids encoding the same. In certain aspects, a transposases for use according to the embodiments is a polypeptide comprising or consisting of a sequence at least 80%, at least 85%, at least 90%, at least 91%, at least 92%, at least 93%, at least 94%, at least 95%, at least 96%, at least 97%, at least 98%, at least 99%, or 100% identical to SEQ ID NO: 1 or SEQ ID NO: 3. In certain aspects, the transposase embodiments may comprise 1, 2, 3, 4, 5, 6, 7, 8, 9 or 10 amino acid substitutions, deletions or insertions relative to the sequences of SEQ ID NO: 1 or SEQ ID NO: 3. For example, transposase polypeptides of the embodiments may be further modified by one or more amino acid substitutions while maintaining their enzymatic activity. In some cases, an amino acid position can be substituted for an amino acid at a corresponding position of a different transposase sequence. For example, the sequence of additional transposases are provided in U.S. Pat. Nos. 6,489,458; 7,148,203; 8,227,432; U.S. Patent Publn. No. 2011/0117072; Mates et al., 2009 and in Ivics et al., 1997, each of which are incorporated herein by reference in their entirety.

In some aspects, amino acid substitutions can be made at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in a transposase and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2, those that are within ±1, and those within ±0.5 comprise contemplated embodiments. Thus, any of the transposase polypeptides described herein may be modified by the substitution of an amino acid, for different, but homologous amino acid with a similar hydrophilicity value. Amino acids with hydrophilicities within +/−1.0, or +/−0.5 points are considered homologous.

In still further aspects, a transposase polypeptide of the embodiments is fused to a heterologous polypeptide sequence, such as a purification tag (e.g., a T7, poly-His or GST tag), a reporter or a CPP. For example the polypeptide may be fused (or conjugated) to a reporter, such as an imaging agent. It will be understood that in certain cases, a fusion protein may comprise additional amino acids positioned between the transposase and a heterologous polypeptide. In general these sequences are interchangeably termed "linker sequences" or "linker regions." One of skill in the art will recognize that linker regions may be one or more amino acids in length and often comprise one or more glycine residue(s) which confer flexibility to the linker. Such linker sequences can be repeated 1, 2, 3, 4, 5, 6, or more times or combined with one or more different linkers to form an array of linker sequences. For instance, in some applications, a linker region may comprise a protease cleavage site (e.g., for the removal of a purification tag or CPP).

As used herein the terms CPP and membrane translocation peptide (MTP) as used interchangeably to refer to peptide sequences that enhance the ability of a polypeptide to be internalized by a cell. Examples for CPPs for use according to the embodiments include, without limitation, peptide segments derived from HIV Tat, herpes virus VP22, the *Drosophila* Antennapedia homeobox gene product, protegrin I, the T1 CPP, the T2 CPP, or the INF7 CPP (see, e.g., U.S. Patent Pub. No. 20140140976, incorporated herein by reference).

III. Cell Engineering

Aspects of the embodiments concern genetic engineering of mammalian cells using transposases of the embodiments. Generally, such methods will involve introducing into cells (i) a first vector encoding the transposase (or a transposase polypeptide) and (ii) a second vector encoding a desired genetic element that is flanked by transposon repeats. Any type of mammalian cell can be genetically engineered by such a method. However, in certain aspects, the cell (cell population) is a stem cell, iPS cell, immune cell or a precursor of these cells. Methods described below address the specific example of T-cell (or other immune cell) engineering for CAR expression. A skilled artisan will, however, recognize that the methodologies could be equally applied to any given cell type or engineering construct.

Thus, in certain embodiments methods are provided for making and/or expanding the antigen-specific redirected T cells that comprises transfecting T cells with an expression vector containing a DNA construct encoding a CAR. Optionally, such cells are stimulated with antigen positive cells, recombinant antigen, or an antibody to the receptor to cause the cells to proliferate.

In another aspect, a method is provided of stably transfecting and re-directing T cells. Such a transfection according to the embodiments can be by any the various transfection techniques that are well known in the art. In some aspects, nucleic acids can be introduced into cells using viral vectors or viral particles. Indeed, most investigators have used viral vectors to carry heterologous genes into T cells. However, in some aspects, transfection of the embodiments does not involve the use of a viral vector. For instance, transfection can be by electroporation, use of charged or uncharged lipids, cationic polymers or polypeptides, salt precipitation or other non-viral nucleic acid transfer (such as, but not limited to sonoporation). In certain aspects, the transfection uses naked DNA (or RNA or protein, in the case of a transposase). By using naked DNA, the time required to produce redirected T cells can be reduced. "Naked DNA" means DNA encoding a CAR is contained in an expression cassette or vector in proper orientation for expression. An electroporation method of embodiments produces stable transfectants that express and carry on their surfaces CAR.

In some aspects, a CAR of the embodiments can be further defined as a "chimeric TCR" means a receptor that is expressed by T cells and that comprises intracellular signaling, transmembrane, and extracellular domains, where the extracellular domain is capable of specifically binding in an MHC unrestricted manner an antigen that is not normally bound by a T-cell receptor in that manner. Stimulation of the T cells by the antigen under proper conditions results in proliferation (expansion) of the cells and/or production of IL-2. The method is applicable to transfection with chimeric TCRs that are specific for any given target antigens, such as chimeric TCRs that are specific for HER2/Neu (Stancovski et al., 1993), ERBB2 (Moritz et al., 1994), folate binding protein (Hwu et al., 1995), renal cell carcinoma (Weitjens et al., 1996), and HIV-1 envelope glycoproteins gp120 and gp41 (Roberts et al., 1994). Other cell-surface target antigens include, but are not limited to, CD20, carcinoembryonic antigen, mesothelin, ROR1, c-Met, CD56, GD2, GD3, alphafetoprotein, CD23, CD30, CD123, IL-11Ralpha, kappa chain, lambda chain, CD70, CA-125, MUC-1, EGFR and variants, epithelial tumor antigen, and so forth.

In certain aspects, T cells for use according to the embodiments are primary human T cells, such as T cells derived from human peripheral blood mononuclear cells (PBMC), PBMC collected after stimulation with G-CSF, bone marrow, or umbilical cord blood. Conditions include the use of mRNA and DNA and electroporation. Following transfection the cells may be immediately infused or may be stored. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric receptor is expanded ex vivo. The clone selected for expansion demonstrates the capacity to specifically recognize and lyse antigen-expressing target cells. The recombinant T cells may be expanded by stimulation with IL-2, or other cytokines (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be deleted on artificial antigen presenting cell or with an antibody, such as alemtuzumab, which binds CD52 on the T cell surface. In a further aspect, the genetically modified cells may be cryopreserved.

T-cell propagation (survival) after infusion may be assessed by: (i) q-PCR and/or digital PCR (e.g., Droplet Digital™ PCR (Bio-Rad, Hercules, Calif.) using primers specific for the transposon and/or CAR; (ii) flow cytometry using an antibody specific for the CAR; and/or (iii) flow cytometry using soluble TAA.

In certain embodiments of the invention, the CAR cells are delivered to an individual in need thereof, such as an individual that has cancer or an infection. The cells then enhance the individual's immune system to attack the respective cancer or pathogenic cells. In some cases, the individual is provided with one or more doses of the antigen-specific CAR T-cells. In cases where the individual is provided with two or more doses of the antigen-specific CAR T-cells, the duration between the administrations should be sufficient to allow time for propagation in the individual, and in specific embodiments the duration between doses is 1, 2, 3, 4, 5, 6, 7, or more days.

A source of allogeneic or autologous T cells that are modified to include both a chimeric antigen receptor (and, in some cases, that lack functional TCR) may be of any kind, but in specific embodiments the cells are obtained from a bank of umbilical cord blood, peripheral blood, human embryonic stem cells, or induced pluripotent stem cells, for example. Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

A pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

A composition of the embodiments can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular pharmacodynamics associated with the pharmaceutical composition in the particular subject.

Desirably an effective amount or sufficient number of the isolated transduced T-cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes about or at least about 10%, about or at least about 20%, about or at least about 30%, about or at least about 40%, about or at least about 50%, about or at least about 60%, about or at least about 70%, about or at least about 80%, about or at least about 90%, about or at least about 95%, about or at least about 98%, or about or a 100% decrease in tumor size when compared to the original or initial (e.g., "therapy day 0") size of the tumor.

Accordingly, the amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

IV. Engineering Constructs

In certain specific aspects, a transposase system of the embodiments is used to engineer a cell with an expression construct ending a selected genetic element. In such aspects, the selected genetic element is flanked by transposon repeats that are functional with a transposase of the embodiments, such as the IR/DR sequences. The selected genetic element may comprise any sequence desired to be transfected into a cell, but in certain aspects the element encodes a polypeptide coding sequence and appropriate expression control sequences for mammalian expression. In some specific aspects, the selected genetic element encodes an antigen binding moiety, such as an antibody, a T-cell receptor or a chimeric antigen receptor (CAR). As used herein, the term "antigen" is a molecule capable of being bound by an antibody or T-cell receptor or CAR.

Thus, embodiments of the present invention involve nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprised of the shared space between one or more antigens. Pattern recognition receptors, such as Dectin-1, may be used to derive specificity to a carbohydrate antigen. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs. Because most sequence variation associated with immunoglobulins and T-cell receptors are found in the CDRs, these regions are sometimes referred to as hypervariable domains. Among these, CDR3 shows the greatest variability as it is encoded by a recombination of the VJ (VDJ in the case of heavy chain and TCR αβ chain) regions.

It is contemplated that the human CAR nucleic acids are human genes to enhance cellular immunotherapy for human patients. In a specific embodiment, the invention includes a full length CAR cDNA or coding region. The antigen binding regions or domain can comprise a fragment of the VH and VL chains of a single-chain variable fragment (scFv) derived from a particular human monoclonal antibody, such as those described in U.S. Pat. No. 7,109,304, incorporated herein by reference or it can comprise any other antigen-binding moiety. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into what has been referred to by Winters as a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

The intracellular signaling domain of a chimeric antigen receptor of the embodiments is responsible for activation of at least one of the normal effector functions of the immune cell in which the chimeric receptor has been placed. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus the term "intracellular signaling domain" refers to the portion of a protein that transduces the effector function signal and directs the cell to perform a specialized function. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal. Examples include the zeta chain of the T-cell receptor or any of its homologs (e.g., eta, delta, gamma, or epsilon), MB1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins can be used, such as FcγRIII and FcεRI. See Gross et al. (1992), Stancovski et al. (1993), Moritz et al. (1994), Hwu et al. (1995), Weijtens et al. (1996), and Hekele et al. (1996) for disclosures of chimeric T cell receptors using these alternative transmembrane and intracellular domains. In certain embodiments, the human CD3 (intracellular domain is used for activation.

The antigen-specific extracellular domain and the intracellular signaling-domain may be linked by a transmembrane domain, such as the human IgG4Fc hinge and Fc regions. Alternatives include the human CD4 transmembrane domain, the human CD28 transmembrane domain, the transmembrane human CD3ζ domain, or a cysteine mutated human CD3ζ domain, or other transmembrane domains from other human transmembrane signaling proteins, such as CD16 and CD8 and erythropoietin receptor. Additional modifications can be added to the transmembrane amino acid sequences.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3 ζ, an additional signal provided by a human costimulatory receptor inserted in a human CAR is important for full activation of T cells and could help improve in vivo persistence and the therapeutic success of the adoptive immunotherapy.

In particular embodiments, the invention concerns isolated nucleic acid segments and expression cassettes incorporating DNA sequences that encode the CAR. Vectors of the present invention are designed, primarily, to deliver desired genes to immune cells, preferably T cells under the control of regulated eukaryotic promoters, for example, MNDU3 promoter, CMV promoter, EF1alpha promoter, or Ubiquitin promoter. Also, the vectors may contain a selectable marker, if for no other reason, to facilitate their manipulation in vitro. In other embodiments, the CAR can be expressed from mRNA in vitro transcribed from a DNA template.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they bind native antigen on the target cell surface in an HLA-independent fashion. For example, several laboratories have reported on scFv constructs fused to sequences coding for the intracellular portion of the CD3 complex's zeta chain (ζ), the Fc receptor gamma chain, and sky tyrosine kinase (Eshhar et al., 1993; Fitzer-Attas et al., 1998). Re-directed T cell effector mechanisms including tumor recognition and lysis by CTL have been documented in several murine and human antigen-scFv: ζ systems (Eshhar, 1997; Altenschmidt et al., 1997; Brocker et al., 1998).

To date non-human antigen binding regions are typically used in constructing a chimeric antigen receptor. A potential problem with using non-human antigen binding regions, such as murine monoclonal antibodies, is the lack of human effector functionality and inability to penetrate into tumor masses. In other words, such antibodies may be unable to mediate complement-dependent lysis or lyse human target cells through antibody-dependent cellular toxicity or Fc-receptor mediated phagocytosis to destroy cells expressing CAR. Furthermore, non-human monoclonal antibodies can be recognized by the human host as a foreign protein, and therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response. Therefore, the use of human antibodies is more preferred because they do not elicit as strong a HAMA response as murine antibodies. Similarly, the use of human sequences in the CAR can avoid immune-mediated recognition and therefore elimination by endogenous T cells that reside in the recipient and recognize processed antigen in the context of HLA.

In some embodiments, the chimeric antigen receptor comprises: a) an intracellular signaling domain, b) a transmembrane domain, and c) an extracellular domain comprising an antigen binding region.

In specific embodiments, intracellular receptor signaling domains in the CAR include those of the T cell antigen receptor complex, such as the zeta chain of CD3, also Fcγ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, one employs any part of the endogenous T cell receptor complex in the intracellular domain. One or multiple cytoplasmic domains may be employed, as so-called third generation CARs have at least two or three signaling domains fused together for additive or synergistic effect, for example.

In certain embodiments of the chimeric antigen receptor, the antigen-specific portion of the receptor (which may be referred to as an extracellular domain comprising an antigen binding region) comprises a tumor associated antigen or a pathogen-specific antigen binding domain including carbohydrate antigen recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR can be co-expressed with a membrane-bound cytokine to improve persistence when there is a low amount of tumor-associated antigen. For example, CAR can be co-expressed with membrane-bound IL-15.

In certain embodiments intracellular tumor associated antigens may be targeted, such as HA-1, survivin, WT1, and p53. This can be achieved by a CAR expressed on a universal T cell that recognizes the processed peptide described from the intracellular tumor associated antigen in the context of HLA. In addition, the universal T cell may be genetically modified to express a T-cell receptor pairing that recognizes the intracellular processed tumor associated antigen in the context of HLA.

The pathogen may be of any kind, but in specific embodiments the pathogen is a fungus, bacteria, or virus, for example. Exemplary viral pathogens include those of the families of Adenoviridae, Epstein-Barr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella*. In one embodiment the pathogen receptor Dectin-1 can be used to generate a CAR that recognizes the carbohydrate structure on the cell wall of fungi. T cells genetically modified to express the CAR based on the specificity of Dectin-1 can recognize *Aspergillus* and target hyphal growth. In another embodiment, CARs can be made based on an antibody recognizing viral determinants (e.g., the glycoproteins from CMV and Ebola) to interrupt viral infections and pathology.

In some embodiments, the pathogenic antigen is an *Aspergillus* carbohydrate antigen for which the extracellular domain in the CAR recognizes patterns of carbohydrates of the fungal cell wall, such as via Dectin-1.

A chimeric immunoreceptor according to the present invention can be produced by any means known in the art, though preferably it is produced using recombinant DNA techniques. A nucleic acid sequence encoding the several regions of the chimeric receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic T-cell line.

As used herein, a nucleic acid construct or nucleic acid sequence or polynucleotide is intended to mean a DNA molecule that can be transformed or introduced into a T cell and be transcribed and translated to produce a product (e.g., a chimeric antigen receptor).

In an exemplary nucleic acid construct (polynucleotide) employed in the present embodiments, the promoter is operably linked to the nucleic acid sequence encoding the chimeric receptor, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon et al. (2003)). The promoter can be constitutive or inducible, where induction is associated with the specific cell type or a specific level of maturation, for example. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld, 2003). Also, it may be further advantageous to use endogenous or exogenous non-coding regions to stabilize the mRNA.

For expression of a chimeric antigen receptor of the present invention, the naturally occurring or endogenous transcriptional initiation region of the nucleic acid sequence encoding N-terminal components of the chimeric receptor can be used to generate the chimeric receptor in the target host. Alternatively, an exogenous transcriptional initiation region can be used that allows for constitutive or inducible expression, wherein expression can be controlled depending upon the target host, the level of expression desired, the nature of the target host, and the like.

Likewise, a signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region may be provided by the naturally occurring or endogenous transcriptional termination region of the nucleic acid sequence encoding the C-terminal component of the chimeric receptor. Alternatively, the termination region may be derived from a different source. For the most part, the source of the termination region is generally not considered to be critical to the expression of a recombinant protein and a wide variety of termination regions can be employed without adversely affecting expression.

The chimeric constructs of the present invention find application in subjects having or suspected of having cancer by reducing the size of a tumor or preventing the growth or re-growth of a tumor in these subjects. Accordingly, the present invention further relates to a method for reducing growth or preventing tumor formation in a subject by introducing a chimeric construct of the present invention into an isolated T cell of the subject and reintroducing into the subject the transformed T cell, thereby effecting anti-tumor responses to reduce or eliminate tumors in the subject. Suitable T cells that can be used include cytotoxic lymphocytes (CTL) or any cell having a T cell receptor in need of disruption. As is well-known to one of skill in the art, various methods are readily available for isolating these cells from a subject. For example, using cell surface marker expression or using commercially available kits (e.g., ISO-CELL™ from Pierce, Rockford, Ill.).

It is contemplated that the chimeric construct can be introduced into the subject's own T cells as naked DNA, combined with other reagents (including but not limited to lipids, cationic polymers, PEG-complexes, protein complexes), or in a suitable vector. Methods of stably transfecting T cells by electroporation using naked DNA are known in the art. See, e.g., U.S. Pat. No. 6,410,319, incorporated herein by reference. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Once it is established that the transfected or transduced T cell is capable of expressing the chimeric receptor as a surface membrane protein with the desired regulation and at a desired level, it can be determined whether the chimeric receptor is functional in the host cell to provide for the desired signal induction. Subsequently, the transduced T cells are reintroduced or administered to the subject to activate anti-tumor responses in the subject. To facilitate administration, the transduced T cells according to the invention can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not ineffectuate the cells expressing the chimeric receptor. Thus, desirably the transduced T cells can be made into a pharmaceutical composition containing a balanced salt solution, preferably Hanks' balanced salt solution, or normal saline.

V. Kits of the Embodiments

Any of the compositions described herein may be comprised in a kit. In some aspects, a transposases polypeptide of the embodiments, or a nucleic acid encoding the same, is provided in the kit. Such a kit may include a variety of additional elements, such a DNA vector encoding transposon repeats, transfection reagents, cells, a CAR expression construct, media, aAPCs, growth factors, antibodies (e.g., for sorting or characterizing CAR T-cells) and/or plasmids encoding CARs or transposase.

In a non-limiting example, a kit comprises a transposases polypeptide of the embodiments, or a nucleic acid encoding the same, one or more reagents to generate a CAR expression construct (having flanking transposon repeats), cells for transfection of the expression construct, and/or one or more instruments to obtain cells for transfection of the expression construct (such an instrument may be a syringe, pipette, forceps, and/or any such medically approved apparatus). In still a further aspects, a transfection device such as an electroporation device is included.

In some embodiments, an expression construct for eliminating endogenous TCR α/β expression, one or more reagents to generate the construct, and/or CAR+ T cells are provided in the kit. In some embodiments, there includes expression constructs that encode zinc finger nuclease(s).

The kits may comprise one or more suitably aliquoted compositions of the present invention or reagents to generate compositions of the invention. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the present invention also will typically include a means for containing the chimeric receptor construct and any other reagent containers in close confinement for commercial sale. Such containers may include injection or blow molded plastic containers into which the desired vials are retained, for example.

VI. Examples

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Recombinant Transposases with High Activity in Human Cells

DNA sequences encoding transposases originally derived from *Salmo salar* (Atlantic salmon) were engineered and humanized in an attempt to produce enzymes with increased efficiency in human cells. The sequences of two of the produced transposases (and their nucleic acid coding sequences) are shown below and have been named as hSB110 and hSB81.

```
hSB110 (SEQ ID NO: 1):
  1  mgkskeisqd  lrkrivdlhk  sgsslgaisk  rlavprssvq tivrkykhhg  ttqpsyrsgr 61  rrvlsprder  tlvrkvqinp  rttakdlvkm  leetgtkvsi stvkrvlyrh  nlkghsarkk 121  pllqnrhkka  rlrfarahgd  kdrtfwrnvl  wsdetkielf ghndhryvwr  kkgeackpkn 181  tiptvkhggg  simlwgcfaa  ggtgalhkid  gimdavqyvd ilkqhlktsv  rklklgrkwv 241  fqhdndpkht  skhvrkwlkd  nkvkvlewps  qspdlnpien lwaelkkrvr  arrptnltql 301  hqlcqeewak  ihpnycgklv  egypkrltqv  kqfkgnatky
``` hSB110 (SEQ ID NO: 2):
```
   1 ATGGGCAAGA GCAAAGAGAT CAGCCAGGAC CTGCGGAAGC
     GGATCGTGGA CCTGCACAAG
  61 AGCGGCTCTA GCCTGGGCGC CATCAGCAAG AGACTGGCCG
     TGCCTAGAAG CAGCGTGCAG
 121 ACCATCGTGC GGAAGTACAA GCACCACGGC ACCACCCAGC
     CCAGCTACAG ATCTGGAAGG
 181 CGGAGAGTGC TGAGCCCCAG GGACGAGAGA ACACTCGTGC
     GCAAGGTGCA GATCAACCCC
 241 CGGACCACCG CCAAGGACCT CGTGAAGATG CTGGAAGAGA
     CAGGCACCAA GGTGTCCATC
 301 AGCACCGTGA AGCGGGTGCT GTACCGGCAC AACCTGAAGG
     GCCACAGCGC CAGAAAGAAG
 361 CCCCTGCTGC AGAACAGACA CAAGAAGGCC CGGCTGAGAT
     TCGCCAGAGC CCACGGCGAC
 421 AAGGACAGAA CCTTCTGGCG GAACGTGCTG TGGAGCGACG
     AGACAAAGAT CGAGCTGTTC
 481 GGCCACAACG ACCACAGATA CGTGTGGCGG AAGAAGGGCG
     AGGCCTGCAA GCCCAAGAAC
 541 ACCATCCCCA CAGTGAAGCA CGGCGGAGGC AGCATCATGC
     TGTGGGGCTG TTTTGCCGCT
 601 GGCGGCACAG GCGCCCTGCA CAAAATCGAC GGCATCATGG
     ACGCCGTGCA GTACGTGGAC
 661 ATCCTGAAGC AGCACCTGAA AACCTCTGTG CGGAAGCTGA
     AGCTGGGCCG GAAATGGGTG
 721 TTCCAGCACG ACAACGACCC CAAGCACACC AGCAAGCACG
     TGCGGAAATG GCTGAAGGAC
 781 AACAAAGTGA AAGTGCTGGA ATGGCCCAGC CAGTCCCCCG
     ACCTGAACCC CATCGAAAAC
 841 CTGTGGGCCG AGCTGAAGAA AAGAGTGCGG GCCAGACGGC
     CCACCAACCT GACACAGCTG
 901 CACCAGCTGT GCCAGGAAGA GTGGGCCAAG ATCCACCCCA
     ACTACTGCGG CAAGCTGGTG
 961 GAAGGCTACC CCAAGAGGCT GACCCAAGTG AAACAGTTCA
     AGGGCAACGC CACCAAGTAC
1021 TGA
``` hSB81 (SEQ ID NO: 3):
```
   1 mgkskeisqd lrkrivdlhk sgsslgaisk rlavprssvq
     tivrkykhhg ttqpsyrsgr
  61 rrvlsprder tlvrkvqinp rttakdlvkm leetgtkvsi
     stvkrvlyrh nlkghsarkk
 121 pllqnrhkka rlrfarahgd kdrtfwrnvl wsdetkielf
     ghndhryvwr kkgeackpkn
 181 tiptvkhggg simlwgcfaa ggtgalhkid gimdavqyvd
     ilkqhlktsv rklklgrkwv
 241 fqhdndpkht skhvrkwlkd nkvkvlewps qspdlnpien
     lwaelkkrvr arrptnltql
 301 hqlcqeewak ihptycgklv egypkrltqv kqfkgnatky
``` hSB81 (SEQ ID NO: 4):
```
   1 ATGGGCAAGA GCAAAGAGAT CAGCCAGGAC CTGCGGAAGC
     GGATCGTGGA CCTGCACAAG
  61 AGCGGCTCTA GCCTGGGCGC CATCAGCAAG AGACTGGCCG
     TGCCTAGAAG CAGCGTGCAG
 121 ACCATCGTGC GGAAGTACAA GCACCACGGC ACCACCCAGC
     CCAGCTACAG ATCTGGAAGG
 181 CGGAGAGTGC TGAGCCCCAG GGACGAGAGA ACACTCGTGC
     GCAAGGTGCA GATCAACCCC
 241 CGGACCACCG CCAAGGACCT CGTGAAGATG CTGGAAGAGA
     CAGGCACCAA GGTGTCCATC
 301 AGCACCGTGA AGCGGGTGCT GTACCGGCAC AACCTGAAGG
     GCCACAGCGC CAGAAAGAAG
 361 CCCCTGCTGC AGAACAGACA CAAGAAGGCC CGGCTGAGAT
     TCGCCAGAGC CCACGGCGAC
 421 AAGGACAGAA CCTTCTGGCG GAACGTGCTG TGGAGCGACG
     AGACAAAGAT CGAGCTGTTC
 481 GGCCACAACG ACCACAGATA CGTGTGGCGG AAGAAGGGCG
     AGGCCTGCAA GCCCAAGAAC
 541 ACCATCCCCA CAGTGAAGCA CGGCGGAGGC AGCATCATGC
     TGTGGGGCTG TTTTGCCGCT
 601 GGCGGCACAG GCGCCCTGCA CAAAATCGAC GGCATCATGG
     ACGCCGTGCA GTACGTGGAC
 661 ATCCTGAAGC AGCACCTGAA AACCTCTGTG CGGAAGCTGA
     AGCTGGGCCG GAAATGGGTG
 721 TTCCAGCACG ACAACGACCC CAAGCACACC AGCAAGCACG
     TGCGGAAATG GCTGAAGGAC
 781 AACAAAGTGA AAGTGCTGGA ATGGCCCAGC CAGTCCCCCG
     ACCTGAACCC CATCGAAAAC
 841 CTGTGGGCCG AGCTGAAGAA AAGAGTGCGG GCCAGACGGC
     CCACCAACCT GACACAGCTG
 901 CACCAGCTGT GCCAGGAAGA GTGGGCCAAG ATCCACCCCA
     CCTACTGCGG CAAGCTGGTG
```

```
 961 GAAGGCTACC CCAAGAGGCT GACCCAAGTG AAACAGTTCA

AGGGCAACGC CACCAAGTAC

1021 TGA
```

Figure 1:
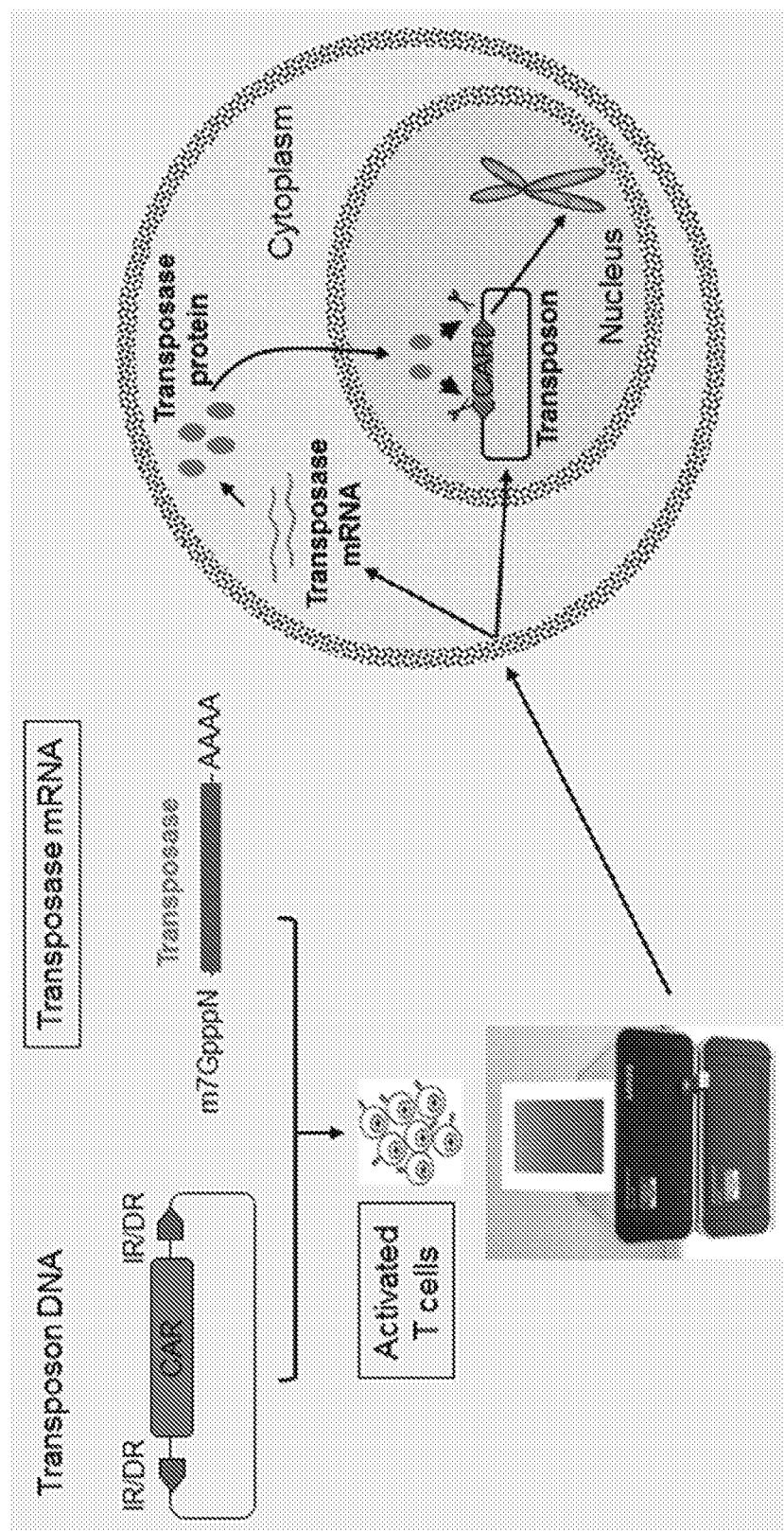
FIG. 1: An exemplary strategy for transposase-based engineering of cells. In this example, engineered T-cells are produced, which express a CAR. T cells are co-transfected with a transposon DNA construct encoding a CAR flanked by transposon repeats along with a mRNA encoding the transposase. In this case, a 4D-NUCLEOFECTOR™ electroporation system (Lonza Group Ltd., Switzerland) is used for the transfection. Once introduced into the cells, the transposase is transiently expressed and mediates integration of the CAR construct into genomic DNA. The mRNA encoding the transposase is degraded within the cells, ensuring no log-term expression of transposase in the cells.

The hSB110 and hSB81 transposases, as well as a control transposase, were then tested for their ability to produce engineered human T-cells with a genetically integrated CAR. The protocol for these studies is shown in FIG. 1. Human T-cells were co-transfected with a transposon DNA construct encoding the CAR flanked by transposon repeats along with a mRNA encoding the transposases polypeptides. For the tranfections a 4D-NUCLEOFECTOR™ electroporation system (Lonza) was used. Following electroporation the cells were cultured and assessed for CAR expression by flow cytometry.

The results of these studies are shown in FIG. 2. The histograms of the upper panels show the number of cells positive for CAR (y-axis) versus cells that have been rendered non-viable, as assessed by 7AAD staining (x-axis), 8-days post transfection. Lower panels show the number of cells positive for CAR (y-axis) and which express CD3 (x-axis), 15-days post transfection. These results clearly demonstrate that the hSB110 and hSB81 transposases are significantly more efficient at engineering cells than SB100x. By day 8 post transfection, over 22% of the hSB110 and hSB81 electroporated cells express CAR. Only 15% of cells from the SB100x electroporation expressed CAR at this time point. No significant difference was seen in the number of non-viable cells with any of the test constructs (as assessed by 7AAD stain). Moreover, by day 15, over 80% of the cell populations electroporated with hSB110 and hSB81 co-expressed CAR and CD3.

All of the methods disclosed and claimed herein can be made and executed without undue experimentation in light of the present disclosure. While the compositions and methods of this invention have been described in terms of certain embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,690,915
U.S. Pat. No. 6,410,319
U.S. Pat. No. 6,489,458
U.S. Pat. No. 7,148,203
U.S. Pat. No. 8,227,432
U.S. Publn. 2011/0117072
U.S. Publn. 2014/0140976

Altenschmidt et al., Adoptive transfer of in vitro-targeted, activated T lymphocytes results in total tumor regression, J Immunol. 1997 Dec. 1; 159(11):5509-15.

Barthel and Goldfeld, *J. Immunol.*, 171:3612-3619, 2003

Brocker et al., *Adv. Immunol.*, 68:257, 1998

Eshhar et al., Specific activation and targeting of cytotoxic lymphocytes through chimeric single chains consisting of antibody-binding domains and the gamma or zeta subunits of the immunoglobulin and T-cell receptors. Proc Natl Acad Sci USA; 90(2):720-4, 1993.

Eshhar, Tumor-specific T-bodies: towards clinical application. Cancer Immunol Immunother. 1997 November-December; 45(3-4):131-6. 1997 Fitzer-Attas et al., Harnessing Syk family tyrosine kinases as signaling domains for chimeric single chain of the variable domain receptors: optimal design for T cell activation. J Immunol. 1998 Jan. 1; 160(1):145-54. 1998

Gross et al., Expression of immunoglobulin-T-cell receptor chimeric molecules as functional receptors with antibody-type specificity. *Proc. Natl. Acad. Sci. USA*, 86:10024-10028, 1989.

Gross et al. (1992) Endowing T cells with antibody specificity using chimeric T cell receptors. FASEB J. 1992 December; 6(15):3370-8.

Hekele et al. Growth retardation of tumors by adoptive transfer of cytotoxic T lymphocytes reprogrammed by CD44v6-specific scFv:zeta-chimera. Int J Cancer. 1996 Oct. 9; 68(2):232-8, 1996.

Hwu et al. (1995) In vivo antitumor activity of T cells redirected with chimeric antibody/T-cell receptor genes. Cancer Res. 1995 Aug. 1; 55(15):3369-73.

Ivics et al., Molecular reconstruction of Sleeping Beauty, a Tc1-like transposon from fish, and its transposition in human cells, *Cell*, 91(4):501-510, 1997.

Kyte and Doolittle, A simple method for displaying the hydropathic character of a protein, J. Mol. Biol., 157(1): 105-32, 1982.

Mates et al., Molecular evolution of a novel hyperactive Sleeping Beauty transposase enables robust stable gene transfer in vertebrates. *Nat. Genetics.* 41(6):753-61, 2009.

Marodon et al., *Blood,* 101:3416-3423, 2003

Moritz et al. (1994) Cytotoxic T lymphocytes with a grafted recognition specificity for ERBB2-expressing tumor cells. *Proc Natl Acad Sci USA.* 1994 May 10; 91(10): 4318-22.

Remington's Pharmaceutical Sciences, 16th Ed., Mack, ed., 1980

Roberts et al., *Blood,* 84:2878, 1994

Stancovski et al., *J. Immunol.*, 151:6577, 1993

Topalian and Rosenberg, 1987

Weijtens et al. (1996) Single chain Ig/gamma gene-redirected human T lymphocytes produce cytokines, specifically lyse tumor cells, and recycle lytic capacity. J Immunol. 1996 Jul. 15; 157(2):836-43.

What is claimed is:

1. A recombinant polypeptide comprising a sequence at least 90% identical to SEQ ID NO: 1, wherein the polypeptide comprises:
   (i) an Arg at the position corresponding to position 14;
   (ii) an Ala at the position corresponding to position 33;
   (iii) a His at the position corresponding to position 115;
   (iv) an Arg at the position corresponding to position 136;
   (v) an Asp at the position corresponding to position 214;
   (vi) an Ala at the position corresponding to position 215;
   (vii) a Val at the position corresponding to position 216;
   (viii) a Gln at the position corresponding to position 217;
   (ix) a His at the position corresponding to position 243;
   (x) a His at the position corresponding to position 253; and
   (xi) an Arg at the position corresponding to position 255, said polypeptide having transposase activity.

2. The polypeptide of claim 1, comprising an Asn at the position corresponding to position 314.

3. The polypeptide of claim 2, wherein the polypeptide is at least 95% identical to the sequence of SEQ ID NO: 1.

4. The polypeptide of claim 2, comprising the sequence of SEQ ID NO: 1.

5. The polypeptide of claim 1, comprising a Thr at the position corresponding to position 314.

6. The polypeptide of claim 5, wherein the polypeptide is at least 90% identical to the sequence of SEQ ID NO: 3.

7. The polypeptide of claim 5, comprising the sequence of SEQ ID NO: 3.

8. A polynucleotide molecule comprising a sequence encoding the polypeptide of claim 1.

9. The polynucleotide molecule of claim 8, wherein the molecule is a mRNA.

10. The polynucleotide molecule of claim 8, wherein the molecule comprises a sequence at least go % identical to SEQ ID NO: 2.

11. The polynucleotide molecule of claim 8, wherein the molecule comprises the sequence of SEQ ID NO: 2.

12. A host cell comprising a polynucleotide encoding the polypeptide of claim 1.

13. The cell of claim 12, wherein the cell is a natural killer (NK) cell, a T-cell or a precursor of aNK cell or T-cell.

14. A method of genetically engineering a cell comprising:
   (a) transfecting the cell with a nucleic acid encoding the polypeptide of claim 1; and a DNA encoding a selected genetic element flanked by transposon repeats; and
   (b) incubating the cell under conditions appropriate for transient or stable transposase activity, thereby integrating the selected genetic element in the genome of the cell and producing an engineered cell.

15. The method of claim 14, wherein the selected genetic element encodes an antibody, a T-cell receptor (TCR), a chimeric antigen receptor (CAR).

16. The method of claim 15, wherein the selected genetic element encodes a CAR.

17. The method of claim 14, wherein transfecting the cell comprises electroporating the cell.

18. The polypeptide of claim 5, wherein the polypeptide is at least 95% identical to the sequence of SEQ ID NO: 3.

19. The polynucleotide molecule of claim 8, wherein the molecule comprises a sequence at least go % identical to SEQ ID NO: 4.

20. The polynucleotide molecule of claim 8, wherein the molecule comprises the sequence of SEQ ID NO: 4.

* * * * *

UNITED STATES PATENT AND TRADEMARK OFFICE
CERTIFICATE OF CORRECTION

PATENT NO. : 10,570,382 B2  
APPLICATION NO. : 15/556868  
DATED : February 25, 2020  
INVENTOR(S) : Laurence J. N. Cooper and Natalya Belousova Page 1 of 1

It is certified that error appears in the above-identified patent and that said Letters Patent is hereby corrected as shown below:

On the Title Page

In Item (56), References Cited, Other Publications, Entry 4, delete "Tcl-like" and insert -- Tc1-like --, therefor.

In the Specification

Column 7, Line 7, delete "Cy" and insert -- Cγ --, therefor.

Column 7, Line 15, delete "Cy" and insert -- Cγ --, therefor.

Column 7, Line 19, delete "Cy" and insert -- Cγ --, therefor.

Column 9, Line 28, delete "meothelin," and insert -- mesothelin, --, therefor.

Column 17, Line 31, delete "(intracellular" and insert -- ζ intracellular --, therefor.

Column 19, Lines 22-23, delete "Picomaviridae," and insert -- Picornaviridae, --, therefor.

Column 26, Line 67, delete "15; 157" and insert -- 15;157 --, therefor.

In the Claims

Column 40, Claim 10, Line 2, delete "go %" and insert -- 90% --, therefor.

Column 40, Claim 13, Line 9, delete "aNK" and insert -- a NK --, therefor.

Column 40, Claim 19, Line 29, delete "go %" and insert -- 90% --, therefor.

Signed and Sealed this  
Twenty-seventh Day of October, 2020

Andrei Iancu  
*Director of the United States Patent and Trademark Office*